United States Patent [19]

Wakimasu et al.

[11] Patent Number: 5,352,659
[45] Date of Patent: Oct. 4, 1994

[54] ENDOTHELIN ANALOGS AND USES THEREOF

[75] Inventors: Mitsuhiro Wakimasu; Takashi Kikuchi; Kazuki Kubo, all of Ibaraki, Japan

[73] Assignee: Takeda Chemical Industries, Osaka, Japan

[21] Appl. No.: 837,780

[22] Filed: Feb. 14, 1992

[30] Foreign Application Priority Data

Feb. 15, 1991 [JP] Japan ................................. 3-022220
Dec. 19, 1991 [JP] Japan ................................. 3-337235

[51] Int. Cl.$^5$ ........................ A61K 37/02; C07K 7/10
[52] U.S. Cl. .......................................... 514/9; 514/13; 530/317; 530/326
[58] Field of Search .................. 530/326, 317; 514/13, 514/9

[56] References Cited

FOREIGN PATENT DOCUMENTS

| | | |
|---|---|---|
| 0436189 | 7/1991 | European Pat. Off. |
| 0499266A1 | 8/1992 | European Pat. Off. ............ 530/326 |
| 3130299 | 8/1989 | Japan . |
| 394692 | 5/1990 | Japan . |
| WO91/13089 | 6/1991 | World Int. Prop. O. |

OTHER PUBLICATIONS

M. Yanigisaw et al., "A Novel Potent Vasoconstrictor Peptide Produced By Vascular Endothelial Cells", *Nature*, 332, (1988), pp. 411–415.

A. Inoue et al, "The Human Endothelin Family" *Proc. Nat'l. Acad. Sci. USA*, 86, (1989) pp. 2863–2867.

C. Hiley et al., "Pressor Effect of Endothelin-1 and Some Analogs in the Perfused Superior Mesenteric Arterial Bed of the Rat" *J. Cardiovascular Pharmacology* 13, Supp. 5, S197–S199 (1989).

K. Nakajima et al., "Structure–Activity Relationship of Endothelin" *Biochemical And Biophysical Research Communications* 163(1), (1989) pp. 424–429.

A. Bdolah et al., "SRTX-d, a new native peptide of the endothelin/sarafatoxin family", FEBS Letters, 256(1,2) (1989) pp. 1–3.

R. de Castiglione et al., "Alanine Scan of Endothelin", in Peptides, Chemistry and Biology, Smith and Rivier (eds.) proc. of the 12th American Peptide Symposium (1992) pp. 402–403.

Erhardt, Paul, *Endothelin*, Chapter 4, p. 52, (Edited by Ruthwayi), 1992, Oxford Press

*Primary Examiner*—Lester L. Lee
*Attorney, Agent, or Firm*—David G. Conlin; Ronald I. Eisenstein

[57] ABSTRACT

Disclosed are a peptide represented by formula (I) or a pharmaceutically acceptable salt thereof:

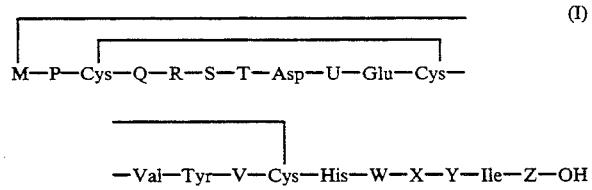

wherein M represents a mercaptoacyl group; P, Q, R, S, T, U, V, W, X, Y and Z each represent amino acid residues, wherein an amino acid side chain of Y is either a substituted saturated aliphatic hydrocarbon group having 1 to 15 carbon atoms or an unsubstituted saturated aliphatic hydrocarbon group having 4 to 15 carbon atoms other than (1S)-1-methylpropyl; (2) a method for producing the above-mentioned peptide or the salt thereof, which comprises subjecting a peptide represented by formula (II) or a salt thereof to an oxidation reaction:

M-P-Cys-Q-R-S-T-Asp-U-Glu-Cys-Val-Tyr-V-Cys-His-W-X-Y-Ile-Z-OH     (II)

wherein M, P, Q, R, S, T, U, V, W, X, Y and Z are as diefined above; and (3) use of the above-mentioned peptide or the pharmaceutically acceptable salt thereof as an anti-endothelin agent.

7 Claims, No Drawings

ENDOTHELIN ANALOGS AND USES THEREOF

BACKGROUND OF THE INVENTION

The present invention relates to novel peptides having antagonistic activity to endothelin receptors. These novel peptides are useful as prophylactic and therapeutic drugs for hypertension, cardiac or cerebral circulatory diseases, renal diseases and asthma, and to the production thereof. The present invention further relates to the use thereof.

Endothelin (ET) is a vasoconstrictive peptide composed of 21 amino acid residues. Endothelin was isolated from the culture supernatant of the endothelial cells of porcine aortas. Its structure was determined by M. Yanagisawa et al. in 1988 [M. Yanagisawa et al., Nature 332, 411–415 (1988)]. More recently, the research on genes coding for endothelin revealed the presence of peptides similar to endothelin in structure. These peptides are named endothelin-1 (ET-1), endothelin-2 (ET-2) and endothelin-3 (ET-3), respectively, and their structures are as follows:

H—Cys—A1—Cys—A2—A3—A4—A5—Asp—Lys—Glu—Cys—Val—Tyr—A6—Cys—His

—Leu—Asp—Ile—Ile—Trp—OH (SEQ ID NO: 3)

|      | A1  | A2  | A3  | A4  | A5  | A6  |            |
|------|-----|-----|-----|-----|-----|-----|------------|
| ET-1 | Ser | Ser | Ser | Leu | Met | Phe | (SEQ ID NO: 4) |
| ET-2 | Ser | Ser | Ser | Trp | Leu | Phe | (SEQ ID NO: 5) |
| ET-3 | Thr | Phe | Thr | Tyr | Lys | Tyr | (SEQ ID NO: 6) |

(All of the amino acids constituting ET-1, ET-2 and ET-3 take the L-form.)

[Inoue et al., Proc. Natl. Acad. Sci. U.S.A. 86, 2863–2867 (1989)]

The above-mentioned peptides of the endothelin family exist in vivo and have vasopressor activity. For this reason, these peptides are anticipated to be intrinsic factors responsible for the control of circulatory systems, and deduced to be related to hypertension, cardiac or cerebral circulatory diseases (for example, cardiac infarction) and renal diseases (for example, acute renal insufficiency). In addition, these peptides also have bronchial smooth muscle constrictor activity, and therefore deduced to be related to asthma.

SUMMARY OF THE INVENTION

It is therefore an object of the present invention to provide novel peptides having antagonistic activity to the endothelin receptors.

The present inventors further studied, the activity of endothelin having strong vascular smooth muscle constrictor activity, and the antagonistic effect of the synthesized novel peptides by amino acid substitution mainly at the 19-position of endothelin.

Namely, the present invention provides (1) a peptide represented by formula (I) (SEQ ID NO: 1) or a pharmaceutically acceptable salt thereof:

M—P—Cys—Q—R—S—T—Asp—U—Glu—Cys— (I)

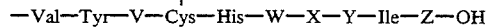

—Val—Tyr—V—Cys—His—W—X—Y—Ile—Z—OH wherein M represents a mercaptoacyl group; P, Q, R, S, T, U, V, W, X, Y and Z each represent amino acid residues, wherein an amino acid side chain of Y is either a substituted saturated aliphatic hydrocarbon group having 1 to 15 carbon atoms or an unsubstituted saturated aliphatic hydrocarbon group having 4 to 15 carbon atoms other than (1S)-1-methylpropyl;

(2) a method of producing the above-mentioned peptide represented by formula (I) or the salt thereof, which comprises subjecting a peptide represented by formula (II) (SEQ ID NO: 2) or a salt thereof to an oxidation reaction:

M-P-Cys-Q-R-S-T-Asp-U-Glu-Cys-Val-Tyr-V-Cys-His-W-X-Y-Ile-Z-OH (II)

wherein M represents a mercaptoacyl group; P, Q, R, S, T, U, V, W, X, Y and Z each represent amino acid residues, wherein an amino acid side chain of Y is either a substituted saturated aliphatic hydrocarbon group having 1 to 15 carbon atoms or an unsubstituted saturated aliphatic hydrocarbon group having 4 to 15 carbon atoms other than (1S)-1-methyl propyl;

(3) a pharmaceutical composition comprising the above-mentioned peptide represented by formula (I) or a pharmaceutically acceptable salt thereof; and (4) use of the above mentioned peptide represented by formula (I) or a pharmaceutically acceptable salt thereof as an anti-endothelin agent.

DESCRIPTION OF THE PREFERRED EMBODIMENTS

In the peptides of the present invention represented by formula (I), the saturated aliphatic hydrocarbon groups with 1 to 15 carbon atoms as the amino acid side chains of Y include alkyl, cycloalkyl or cycloalkyl-alkyl groups in which the alkyl groups may be straight or branched. As alkyl groups, preferred are $C_{1-10}$ alkyl groups, which include, for example, methyl, ethyl, n-propyl, isopropyl, n-butyl, isobutyl, sec-butyl, t-butyl, n-pentyl, isopentyl, neopentyl, n-hexyl, n-heptyl, n-octyl, n-nonyl and n-decyl. As cycloalkyl groups, preferred are $C_{3-10}$ cycloalkyl groups, which include, for example, cyclopropyl, cyclobutyl, cyclopentyl, cyclohexyl, cycloheptyl, cyclooctyl and norbornyl. As cycloalkyl-alkyl groups, preferred are $C_{3-10}$cycloalkyl-$C_{1-6}$alkyl groups, which include, for example, cyclopropylmethyl, cyclobutylmethyl, cyclopentylmethyl, cyclohexylmethyl, cycloheptylmethyl, 1-cyclopentylethyl, 1-cyclohexylethyl, 2-cyclopentylethyl, 2-cyclohexylethyl, 3-cyclohexylpropyl, 4-cyclohexylbutyl and 5-cyclohexylpropyl.

The above-mentioned saturated hydrocarbon groups may also be substituted, and the substituent groups include sulfur-containing groups (such as thione, mercapto, methylthio, ethylthio, n-propylthio, isopropylthio, n-butylthio, isobutylthio, t-butylthio, phenylthio, cyclopentylthio, cyclohexylthio and thienyl), oxygen-containing substituents (such as ketone, hydroxy, methoxy, ethoxy, n-propoxy, isopropoxy, n-butoxy, isobutoxy, t-butoxy, n-pentyloxy, cyclohexyloxy, phenoxy, benzyloxy and furyl), nitrogen-containing groups (such as amino, N-methylamino, N-ethylamino, N-n-propylamino, N-isopropylamino, N-n-butylamino, N-isobutylamino, N-t-butylamino, N-n-pentylamino, N-n-hexylamino, N-cyclohexylamino, N,N-dimethylamino, N,N-diethylamino, N,N-di-n-propylamino, N,N-di-isopropylamino, N,N-di-n-butylamino, N,N-diisobutylamino, N,N-di-t-butylamino, N,N-di-n-pentylamino, N,N-di-n-hexylamino, N,N-dicyclohexylamino, nitro, guanidino, pyrrolidino, piperidino, indolyl and imidazolyl), aromatic hydrocarbon group (such as phenyl, 1-naphtyl, 2-naphtyl) and halogen groups (such as chloro, bromo and fluoro).

The unsubstituted saturated aliphatic hydrocarbon groups with 4 to 15 carbon atoms other than (1S)-1-methylpropyl as the amino acid side chains of Y, are alkyl, cycloalklyl or cycloalkyl-alkyl groups in which alkyl may be straight or branched. As alkyl groups, preferred are $C_{4-10}$ alkyl groups, which include, for example, n-butyl, isobutyl, t-butyl, n-pentyl, isopentyl, neopentyl, n-hexyl, n-heptyl, n-octyl, n-nonyl and n-decyl. As cycloalkyl groups, preferred are $C_{4-10}$ cycloalkyl groups, which include, for example, cyclobutyl, cyclopentyl, cyclohexyl, cycloheptyl, cyclooctyl and norbornyl. As cycloalkyl-alkyl groups, preferred are $C_{3-10}$cycloalkyl-$C_{1-6}$alkyl groups, which include, for example, cyclopropylmethyl, cyclobutylmethyl, cyclopentylmethyl, cyclohexylmethyl, cycloheptylmethyl, 1-cyclopentylethyl, 1-cyclohexylethyl, 2-cyclopentylethyl, 2-cyclohexylethyl, 2,2-dicyclopentylethyl, 2,2-dicyclohexylethyl, 3-cyclohexylpropyl, 4-cyclohexylbutyl and 5-cyclohexylpropyl.

As an amino acid side chain of Y, a hydrocarbon group branched at its β-positioned carbon atom is more preferred, for example, isobutyl, neopentyl, cyclopropylmethyl, cyclobutylmethyl, cyclopentylmethyl, cyclohexylmethyl, cycloheptylmethyl, 2-cyclohexylpropyl, 2,2-dicyclohexylethyl, 2-mercaptopropyl, 2-thienylmethyl, 2-hydroxypropyl, 2-furylmethyl, 3-indolylmethyl, 4-imidazolylmethyl and benzyl.

In this specification, amino acids and peptides are indicated by the abbreviations commonly used in the art or adopted by the IUPAC-IUB Commission on Biochemical Nomenclature. For example, the following abbreviations are used:

Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
Tyr(Et): O-Ethyltyrosine
Nal(1): 1-Naphthylalanine
Nal(2): 2-Naphthylalanine
Cha: Cyclohexylalanine
Thi: β-2-Thienylalanine
Phe(4F): 4-Fluorophenylalanine
Phg: Phenylglycine
Cyt: Cystine
Abu: 2-Aminobutyric acid
Nva: Norvaline
Nle: Norleucine
tLeu: tert-Leucine
γLeu: γ-Methylleucine
Mpr: 3-Mercaptopropionic acid Protective groups and reagents commonly used in this specification are indicated by the following abbreviations:

Boc: t-Butoxycarbonyl
Bzl: Benzyl
BrZ: 2-Bromobenzyloxycarbonyl
ClZ: 2-Chlorobenzyloxycarbonyl
Tos: p-Toluenesulfonyl
Dnp: 2,4-Dinitrophenyl
OcHex: Cyclohexyl ester
For: Formyl
MeBzl: 4-Methylbenzyl
Acm: Acetamidomethyl
TFA: Trifluoroacetic acid
HF: Anhydrous hydrogen fluoride
HOBt: 1-Hydroxybenzotriazole
DMF: N,N-Dimethylformamide In the present invention, the mercaptoacyl groups represented by M which may be substituted are carboxylic acid-derived acyl groups having mercapto groups, which include aliphatic, alicyclic and aromatic carboxylic acids. Preferred examples of the aliphatic mercaptoacyl groups include mercapto $C_2$–$C_{10}$ alkanoyl groups such as 3-mercaptopropionyl and 4-mercaptobutyryl. Preferred examples of the alicyclic mercaptoacyl groups include mercapto $C_3$–$C_8$ cycloalkylcarbonyl groups such as 3-mercaptocyclopentylcarbonyl. Preferred examples of the aromatic mercaptoacyl groups include $C_6$–$C_{14}$ arylcarbonyl groups such as 3-mercapto-3-phenylpropionyl. The above-mentioned aliphatic and alicyclic groups are preferably used. As noted above, the mercaptoacyl groups may be substituted. Substituent groups on the mercaptoacyl groups include amino and hydroxyl groups. A mercaptoacyl group substituted by an amino group at the α-position of the acyl group is more preferred. Preferred examples thereof include Cys, homocysteine and 3-mercapto-D-valine (penicillamine). The most preferred examples of the unsubstituted mercaptoacyl groups and the substituted mercaptoacyl groups are 3-mercaptopropionyl and Cys, respectively.

In the present invention, the amino acid residue represented by P, Q, R, S, T, U, V, W, X, Y or Z may be either a natural amino acid residue or a synthetic amino acid residue, and may be any of the L-, D- and DL-forms. Accordingly, P, Q, R, S, T, U, V, W, X, Y and Z can also be expressed as

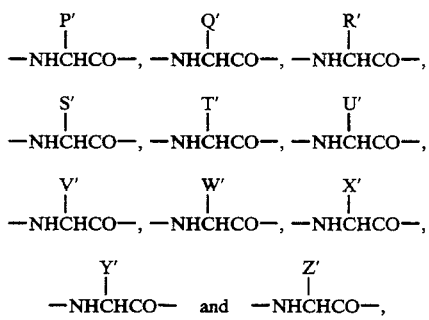

respectively. The compound of formula (I) (SEQ ID NO: 1) can therefore be represented by formula (I') (SEQ ID NO: 1):

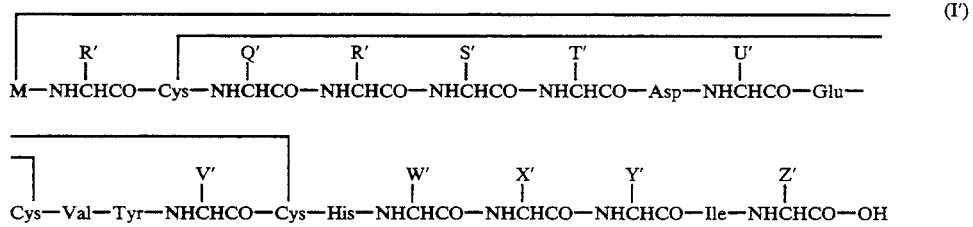

wherein P', Q', R', S', T', U', V', W', X' and Z' each represent hydrogen atoms or hydrocarbon groups with 1 to 15 carbon atoms which may be substituted, and Y' represents either a substituted saturated aliphatic hydrocarbon group having 1 to 15 carbon atoms or an unsubstituted saturated aliphatic hydrocarbon group having 4 to 15 carbon atoms other than (1S)-1-methylpropyl. The hydrocarbon groups having 1 to 15 carbon atoms include aliphatic hydrocarbon groups, aromatic hydrocarbon groups and aliphatic-aromatic hydrocarbon groups.

The aliphatic hydrocarbon groups represented by P' to X' and Z' described above may be straight, branched or cyclic groups which may be saturated. Examples thereof include methyl, ethyl, n-propyl, isopropyl, n-butyl, isobutyl, sec-butyl, t-butyl, n-pentyl, isopentyl, neopentyl, cyclopentyl, n-hexyl, cyclohexyl, n-heptyl, cycloheptyl, n-octyl, n-nonyl, n-decyl, cyclopentylmethyl and cyclohexyl-methyl. The substituted aliphatic hydrocarbon groups include methylthiomethyl, ethylthiomethyl, n-propylthiomethyl, isopropylthiomethyl, n-butylthiomethyl, t-butylthiomethyl, 2-methylthioethyl, 2-ethylthioethyl, 2-t-butylthioethyl, mercaptomethyl, 1-mercaptoethyl, 2-mercaptoethyl, phenylthiomethyl, 1-phenylthioethyl, 2-phenylthioethyl, benzylthiomethyl, 4-methoxyphenylthiomethyl, 4-methoxybenzylthiomethyl, 4-methylbenzylthiomethyl, 4-nitrobenzylthiomethyl, 4-pyridylbenzylthiomethyl, hydroxymethyl, 1-hydroxyethyl, 2-hydroxyethyl, methoxy-methyl, ethoxymethyl, n-propoxymethyl, isopropoxymethyl, n-butoxymethyl, t-butoxymethyl, n-pentyloxymethyl, cyclo-pentyloxymethyl, n-hexyloxymethyl, cyclohexyloxlnethyl, 1-methoxyethyl, 1-ethoxyethyl, 1-propoxyethyl, 1-isopropoxyethyl, 1-n-butoxyethyl, 1-isobutoxyethyl, 1-t-butoxyethyl, phenoxymethyl, 1-phenoxyethyl, 2-phenoxyethyl, benzyloxymethyl, 2-benzyloxyethyl, carboxymethyl, 1-carboxyethyl, 2-carboxyethyl, methoxycarbonylmethyl, ethoxycarbonylmethyl, n-propoxycarbonylmethyl, isopropoxycarbonylmethyl, n-butoxycarbonylmethyl, isobutoxycarbonylmethyl, t-butoxycarbonylmethyl, n-pentyloxycarbonylmethyl, cyclopentyloxycarbonylmethyl, n-hexyloxycarbonylmethyl, cyclohexyloxycarbonylmethyl, cycloheptyloxycarbonylmethyl, cyclooctyloxycarbonylmethyl, carboxyethyl, methoxycarbonylethyl, ethoxycarbonylethyl, n-propoxycarbonylethyl, isopropoxycarbonylethyl, n-butoxycarbonylethyl, isobutoxycarbonylethyl, t-butoxycarbonylethyl, n-pentyloxycarbonylethyl, cyclopentyloxycarbonylethyl, n-hexyloxycarbonylethyl, cyclohexyloxycarbonylethyl, cycloheptyloxycarbonylethyl, cyclooctyloxycarbonylethyl, 2-aminoethyl, 2-(N-methylamino)ethyl, 2-(N,N-dimethylamino)ethyl, 3-aminopropyl, 3-(N,N-diethylamino)propyl, 2-guanidinoetyl, 3-guanidinopropyl, aminocarbonylmethyl, N-methylaminocarbonylmethyl, N-ethylaminocarbonylmethyl, N-n-propyl-aminocarbonylmethyl, N-isopropylaminocarbonylmethyl, N-n-butylaminocarbonylmethyl, N-isobutylaminocarbonylmethyl, N-t-butylaminocarbonylmethyl, N-n-pentylamino-carbonylmethyl, N-isopentylaminocarbonylmethyl, N-neopentylaminocarbonylmethyl, N-n-hexylaminocarbonylmethyl, N-cyclohexylaminocarbonylmethyl, N,N-dimethylaminocarbonylmethyl, N,N-diethylaminocarbonylmethyl, N,N-di-n-propylaminocarbonylmethyl, N,N-diisopropylaminocarbonylmethyl, N,N-di-n-butylaminocarbonylmethyl, N,N-diisobutylaminocarbonylmethyl, N,N-di-t-butylaminocarbonylmethyl, N,N-di-n-pentylaminocarbonylmethyl, N,N-diisopentylaminocarbonylmethyl, N,N-dineopentylaminocarbonylmethyl, N,N-di-n-hexylaminocarbonylmethyl, N,N-dicyclohexylaminocarbonylmethyl, pyrrolidinocarbonylmethyl, piperidinocarbonylmethyl, aminocarbonylethyl, N-methylaminocarbonylethyl, N-ethylaminocarbonylethyl, N-n-propylaminocarbonylethyl, N-isopropylaminocarbonylethyl, N-n-butylaminocarbonylethyl, N-isobutylaminocarbonylethyl, N-t-butylaminocarbonylethyl, N-n-pentylaminocarbonylethyl, N-cyclopentylaminocarbonylethyl, N-n-hexylaminocarbonylethyl, N-cyclohexylaminocarbonylethyl, N,N-dimethylaminocarbonylethyl, N,N-diethylaminocarbonylethyl, N,N-di-n-propylaminocarbonylethyl, N,N-diisopropylaminocarbonylethyl, N,N-di-n-butylaminocarbonylethyl, N,N-diisobutylaminocarbonylethyl, N,N-di-t-butylaminocarbonylethyl, N,N-di-n-pentylaminocarbonylethyl, N,N-dicyclopentylaminocarbonylethyl, N,N-di-n-hexylaminocarbonylethyl, N,N-dicyclohexylaminocarbonylethyl, 3-indolylmethyl, 4-imidazolylmethyl, 2-thienylmethyl, 2-furylmethyl, pyrrolidinocarbonylethyl and piperidinocarbonylethyl.

Examples of the aromatic hydrocarbon groups and aliphatic-aromatic hydrocarbon groups represented by P' to X' and Z' include phenyl, 1-naphthyl, 2-naphthyl, phenylmethyl, 1-phenylethyl, 2-phenylethyl, 1-naphthylmethyl, 2-naphthylmethyl and 9-anthranylmethyl. Examples of the substituted aromatic hydrocarbon groups and aliphatic-aromatic hydrocarbon groups include 4-hydroxyphenyl, 4-hydroxyphenylmethyl, 4-methoxyphenylmethyl, 4-ethoxyphenylmethyl, 4-n-propoxyphenylmethyl, 4-isopropoxyphenylmethyl, 4-n-butoxyphenylmethyl, 4-isobutoxyphenylmethyl, 4-t-butoxyphenylmethyl, 4-n-pentyloxyphenylmethyl, 4-cyclopentyloxyphenylmethyl, 4-n-hexyloxyphenylmethyl, 4-cyclohexyloxyphenylmethyl, 4-aminophenylmethyl, 4-dimethylaminophenylmethyl, 4-diethylaminophenylmethyl, 4-di-n-propylaminophenylmethyl, 4-diisopropylaminophenylmethyl, 4-di-n-butylaminophenylmethyl, 4-pyrrolidinophenylmethyl, 4-piperidinophenylmethyl, 4-nitrophenylmethyl, 4-fluorophenylmethyl, 3-fluorophenylmethyl, 2-fluorophenylmethyl, 4-chlorophenylmethyl, 3-chlorophenylmethyl and 2-chlorophenylmethyl.

Y' corresponds to the amino acid side chain of Y as described above. Therefore, Y' has the same meaning as the amino acid side chain of Y, and represents a substituted saturated aliphatic hydrocarbon group having 1 to 15 carbon atoms or an unsubstituted saturated aliphatic hydrocarbon group having 4 to 15 carbon atoms other than (1S)-1-methylpropyl.

Preferred examples of the amino acid residues represented by P to Z (having P' to Z', respectively) are more specifically described below.

P is an amino acid residue having an alkyl group which may be substituted as the amino acid side chain (P'). And hydroxy group is preferred as this substituent group. Specific examples of the substituent groups include Ala as well as Ser and Thr.

Q includes, for example, Ser, Thr, Phe and Ala. Ser and Ala are preferred among others.

R is an amino acid residue having an alkyl group which may be substituted as the amino acid side chain (R'). A OH is preferred as this substituent group. Specific examples of the substituent groups include Ala as well as Ser and Thr.

S is an amino acid residue having a lipophilic portion as the amino acid side chain (S'). Specific examples thereof include Leu, Ala, Tyr, Trp and Met, and Leu is preferred.

T includes Met, Leu, Lys, Ala, Nle and Glu, and Met, Ala and Nle are preferred.

U includes Lys, Ala and Glu.

As V, aromatic amino acids are preferred, with the monocyclic ones preferred over the bicyclic ones. Preferred examples thereof include Trp as well as Phe and Tyr.

W includes Gln as well as Leu.

As Z, aromatic amino acids are preferred, with bicyclic ones being more preferred. Preferred examples thereof include Trp, and Trp having a substituent group [for example, N-(indole)-formyltryptophan], α-naphthylalanine and β-naphthylalanine. Substituted compounds such as N-(indole)-formyl compounds are often used in place of tryptophan easily decomposed by oxidation.

As X, amino acid residues other than Asp are preferred, and particularly, amino acid residues having hydroxyl groups are preferred due to their strong binding affinity for endothelin receptors. Preferred examples thereof include Ser and Thr. In addition, amino acid residues such as Asn and Gly are also preferably used.

Preferred examples of Y include amino acid residues having the amino acid side chain (Y') branched at the 2-position, for example, Leu, Cha, Phe, γLeu and Asn.

Although embodiments of the present invention have emphasized substitution of (Y) at the 19-position, further substitution at the 18-position is also within the scope of the invention. Preferred combinations of the 18-position and the 19-position include Thr-Leu, Thr-γLeu, Thr-Cha, Thr-Phe, Thr-Asn, Ser-Leu, Asn-Leu and Gly-Leu. The combinations of Thr-Leu, Thr-γLeu and Thr-Cha are especially preferred.

The pharmaceutically acceptable salts of the peptides represented by formula (I) or (I') include sodium salts, potassium salts and calcium salts as well as addition salts of inorganic acids such as hydrochlorides, sulfates and phosphates, and salts of organic acids such as acetates, propionates, citrates, tartarates, malates and oxalates.

The peptides of the present invention represented by formula (I) or (I') can be produced by methods for peptide synthesis known in the art, which may be either solid phase synthesis methods or liquid phase synthesis methods. Examples of such methods for peptide synthesis include methods described in M. Bodansky and M. A. Ondetti, *Peptide Synthesis*, Interscience, New York (1966); F. M. Finn and K. Hofmann, *The Proteins*, Vol. 2, edited by H. Nenrath and R. L. Hill, Academic Press, New York, (1976); N. Izumiya et al., *Peptide Gosei no Kiso to Jikken (Fundamentals and Experiments of Peptide Synthesis)*, Maruzen (1985); H. Yazima, S. Sakakibara et al., *Seikagaku Jikken Koza (Course of Biochemical Experiments)*, 1, edited by Biochemical Society of Japan, Tokyo Kagaku Dojin (1977); H. Kimura et al., *Zoku Seikagaku Jikken Koza (Course of Biochemical Experiments, second series)*, 2, edited by Biochemical Society of Japan, Tokyo Kagaku Dojin (1987); and J. M. Stewart and J. D. Young, *Solid Phase Peptide Synthesis*, Pierce Chemical Company, Illinois (1984), which describe azide methods, chloride methods, acid anhydride methods, mixed acid anhydride methods, DCC methods, active ester methods, methods using Woodward reagent K, carbodiimidazole methods, oxidation-reduction methods, DCC/HONB methods and methods using BOP reagents.

The peptides of the present invention represented by formula (I) or (I') can be produced by condensing a raw material having a reactive carboxyl group corresponding to one of two kinds of fragments which are separated at any position of its peptide bond with a raw material having a reactive amino group corresponding to the other fragment, and then, eliminating a protective group by methods known in the art, if the resulting condensed product has any protective group, followed by further oxidation reaction.

In particular, in the solid phase synthesis methods, an amino acid whose functional groups which should not affect the reaction are protected, is combined with an insoluble resin such as a Pam resin through the carboxyl group of the amino acid. After elimination of the $N^\alpha$-protective group, an amino acid, whose functional groups which should not affect the reaction are protected, is condensed therewith. This procedure is repeated until a desired protected peptide is obtained. Then, the protective group is eliminated and the desired peptide is released from the resin by methods known in the art such as hydrogen fluoride treatment, trifluoromethanesulfonic acid treatment and trifluoroacetic acid treatment, followed by further oxidation reaction, whereby the compound of the present invention is produced.

When the M¹-Cys¹⁵ and Cys³-Cys¹¹ bonds are formed by the oxidation reaction, a compound represented by formula (II) or (II') is oxidized by methods known in the art.

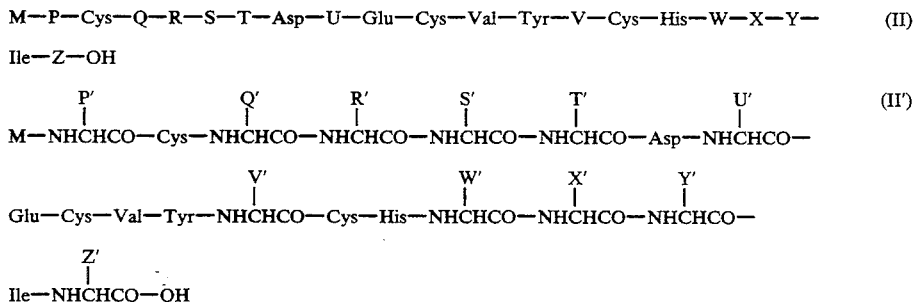

In this case, (1) the two di-sulfide bonds may be concurrently formed by the oxidation reaction, (2) the oxidation reaction may be conducted with the protective groups of M¹ and Cys¹⁵ to form the Cys³-Cys¹¹ bond, and then the protective groups may be eliminated, followed by further oxidation to form the M¹-Cys¹⁵ bond, or (3) the oxidation reaction may be conducted with the protective groups of Cys³ and Cys¹¹ to form the M¹-Cys¹⁵ bond, and then the protective groups may be eliminated, followed by further oxidation to form the Cys³-Cys¹¹ bond.

Protection of the functional groups which should not affect the reaction of the raw materials, the protective groups, elimination of the protective groups, and activation of the functional groups related to the reaction can also be suitably selected from groups or methods known in the art.

Examples of the protective groups for the amino group of the raw materials include carbobenzoxy, t-butyloxycarbonyl, t-amyloxycarbonyl, isobornyloxycarbonyl, 4-methoxybenzyloxycarbonyl, 2-chlorobenzyloxycarbonyl, adamantyloxycarbonyl, trifluoroacetyl, phthalyl, formyl, 2-nitrophenylsulfenyl, diphenylphosphinothioyl and 9-fluorenylmethyloxycarbonyl. The protective groups for the carboxyl group include, for example, alkyl esters (such as esters of methyl, ethyl, propyl, butyl, t-butyl, cyclopentyl, cyclohexyl, cycloheptyl, cyclooctyl and 2-adamantyl), benzyl esters, 4-nitrobenzyl esters, 4-methoxybenzyl esters, 4-chlorobenzyl esters, benzhydryl esters, phenacyl esters, carbobenzoxyhydrazide, t-butyloxycarbonylhydrazide and tritylhydrazide.

Examples of the protective groups for the thiol group of cysteine include 4-methoxybenzyl, 4-methylbenzyl, benzyl, t-butyl, adamantyl, trityl, acetamidomethyl, carbomethoxysulfenyl, 3-nitro-2-pyridinesulfenyl and trimethylacetamidomethyl.

The hydroxyl group of serine can be protected, for example, by esterification or etherification. Examples of groups suitable for this esterification include lower alkanoyl groups such as acetyl, aroyl groups such as benzoyl, and carbonic acid-derived groups such as benzyloxycarbonyl and ethyloxycarbonyl. Examples of groups suitable for the etherification include benzyl, tetrahydropyranyl and t-butyl. However, the hydroxyl group of serine is not always required to be protected.

Examples of the protective groups for the phenolic hydroxyl group of tyrosine include benzyl, 2,6-dichlorobenzyl, 2-nitrobenzyl, 2-bromobenzyloxycarbonyl and t-butyl. However, the phenolic hydroxyl group of tyrosine is not always required to be protected.

Methionine may be used in the form of sulfoxides.

The protective groups for the imidazole ring of histidine include p-toluenesulfonyl, 4-methoxy-2,3,6-trimethylbenzenesulfonyl, 2,4-dinitrophenyl, benzyloxymethyl, t-butoxymethyl, t-butoxycarbonyl, trityl and 9-fluorenylmethyloxycarbonyl. However, the imidazole ring is not always required to be protected.

The protective groups for the indole ring of tryptophan include formyl, 2,4,6-trimethylbenzensulfonyl, 2,4,6-trimethoxybenzenesulfonyl, 4-methoxy-2,3,6-trimethylbenzenesulfonyl, β,β,β-trichloroethyloxycarbonyl and diphenylphosphinothioyl. However, the indole ring is not always required to be protected.

Examples of the reactive carboxyl groups of the raw materials include the corresponding acid anhydrides, azide and active esters (esters of alcohols such as pentachlorophenol, 2,4,5-trichlorophenol, 2,4-dinitrophenol, cyanomethyl alcohol, p-nitrophenol, N-hydroxy-5-norbornene-2,3-dicarboxyimide, N-hydroxysuccinimide, N-hydroxyphthalimide and N-hydroxybenzotriazole. Examples of the activated amino acid groups of the raw materials include the corresponding phosphoric acid amides.

Condensation reaction can be conducted in the presence of a solvent(s). The solvent(s) can be appropriately selected from the solvents commonly used in peptide condensation reactions. Examples of the solvents include anhydrous or hydrous dimethylformamide, dimethyl sulfoxide, pyridine, chloroform, dioxane, dichloromethane, tetrahydrofuran, acetonitrile, ethyl acetate, N-methylpyrrolidone and appropriate mixtures thereof.

The reaction temperature is appropriately selected from the temperature range commonly used in peptide bond-forming reactions, usually from the range of about −20° to about 30° C.

After protection is accomplished, the protected peptide or the protected peptide resin thus obtained is subjected to protective group-eliminating reaction. Although this reaction varies depending on the kind of protective group, it is in any event industrially advantageous to eliminate all protective groups in one step without affecting the peptide bonds. As to the cysteine-containing peptides, it is more advantageous from the viewpoint of ease of purification to eliminate the protective groups in two steps, namely, to eliminate the protective groups other than the protective groups for the thiol group first, followed by elimination of the protective groups for the thiol group. The protective groups for the thiol group used in such cases include acetamidomethyl and trimethyl-acetamidomethyl.

As described above, in the oxidation reaction of the final stage, the peptide represented by formula (II) or (II') from which all of the protective groups are eliminated may be oxidized in one step to produce the peptide represented by formula (I) or (I'). Alternatively, the peptide represented by formula (II) or (II') where only two mercapto group are protected, is subjected to the first oxidation, and then the protective groups may be eliminated, followed by the second oxidation to produce the peptide represented by formula (I) or (I'). In the latter case, the oxidative deprotecting reaction is also usable, in which the elimination of the protective groups and the oxidation of the resulting thiol groups may be conducted in a single reaction. Further, since Trp is easy to be oxidized as described above, the above-mentioned oxidation reaction may also be conducted before the protective groups for Trp in the molecule are eliminated. Thereafter, the protective groups for Trp are eliminated.

Methods for eliminating the protective groups include, for example, reduction with sodium in liquid ammonia, in addition to acid treatment with anhydrous hydrogen fluoride, methanesulfonic acid, trifluoromethanesulfonic acid, trifluoroacetic acid or mixtures thereof. The protective group-eliminating reaction by the above-mentioned acid treatment is generally conducted at a proper temperature between about $-20°$ and about $40°$ C. In the acid treatment, it is effective to add a cation trapping agent such as anisole, phenol, thioanisole, m-cresol, p-cresol, dimethylsulfide, 1,4-butanedithiol or 1,2-ethanedithiol. For the protective groups for the thiol group which are stable to the acid treatment, acetamidomethyl and 3-nitro-2-pyridinesulfenyl groups are available, and the former can be eliminated with iodine or mercury acetate, and the latter can be eliminated with mercaptoethanol. The 2,4-dinitrophenyl group used as the protective group for the imidazole ring of histidine is eliminated by thiophenol treatment. The formyl group used as the protective group for the indole ring of tryptophan may be eliminated by either (i) alkali treatment using dilute sodium hydroxide, dilute ammonia or the like, or (ii) the above-mentioned elimination by the acid treatment in the presence of 1,2-ethanedithiol, 1,4-butanedithiol or the like.

When the peptide obtained by eliminating the protective groups of the protected peptide in this manner is the thiol peptide represented by formula (II) or (II'), the thiol peptide is subjected to oxidation. Preferred oxidation methods include the methods of oxidizing the thiol peptide in a solvent such as water with air, potassium ferricyanide, iodine, diiodoethane or the like. It is desirable that the above-mentioned oxidation reaction be generally conducted at a high dilution, at a proper temperature of about $0°$ to about $40°$ C., at a pH of about 6 to about 8.5.

After completion of the reaction, the peptide represented by formula (I) or (I') thus obtained is collected by conventional separation methods of peptide such as extraction, distribution, reprecipitation, recrystallization, column chromatography and high performance liquid chromatography.

The peptide of the present invention represented by formula (I) or (I') may also be obtained by methods known in the art as salts such as the sodium salt, the potassium salt, the calcium salt and the magnesium salt, or as acid addition salts, particularly pharmaceutically acceptable acid addition salts. Examples thereof include salts of inorganic acids (such as hydrochloric acid, sulfuric acid and phosphoric acid) or organic acids (such as acetic acid, propionic acid, citric acid, tartaric acid, malic acid, oxalic acid and methanesulfonic acid).

The peptides of the present invention or the pharmaceutically acceptable salts thereof bind to endothelin receptors of warm-blooded animals as shown in the experimental examples described below, but do not exhibit endothelin-like constrictor activity. Therefore, they function as endothelin antagonists. To bring about an anti-endothelin activity in warm-blooded animals, an effective amount of the peptides or the pharmaceutically acceptable salts thereof is administered to the warm-blooded animals.

The novel peptides of the present invention in which any amino acids are substituted at the 1-, 2-, 4-, 5-, 6-, 7-, 9-, 14-, 17- 18- 19- and 21 positions of endothelin, particularly at the 19-position, have the remarkable effect of suppressing the vasopressor activity of endothelin as the endothelin antagonists. Thus, the novel peptides of the present invention or the salts thereof are the endothelin antagonists having vasodilator activity, so that they can be used as agents for improving circulatory functions or therapeutic agents for cardiac infarction, acute renal insufficiency, asthma and the like.

The novel peptides of the present invention, when used as the above-mentioned therapeutic drugs, can be safely administered orally or parenterally in the form of powders, granules, tablets, capsules, injections, suppositories, ointments or sustained release preparations, alone or in combination with pharmaceutically acceptable carriers, excipients or diluents. The peptides of the present invention are typically administered parenterally, for example, by intravenous or subcutaneous injection, intraventricular or intraspinal administration, nasotracheal administration or intrarectal administration. In some cases, however, they are administered orally.

The peptides of the present invention are stable substances, and therefore, can be stored as physiological saline solutions. It is also possible to lyophilize the peptides, store them in ampules with mannitol or sorbitol, and dissolve them in a suitable carrier. The peptides of the present invention can be given in their free forms, or in the form of alkali addition salts or acid addition salts thereof. Both of the free peptides represented by formula (I) and the alkali addition salts or the acid addition salts thereof are generally given in a proper dose within the range of 1 ng to 10 mg of free peptid per kg of weight.

More specifically, the dosage varies depending on the type of disease to be treated, the symptom of the disease, the object to which the drugs are given and the route of administration. For example, when given by injection to adult patients of hypertension, it is advantageous that the active ingredients (the compounds represented by formula (I)) are normally given in one dose of about 1 ng to 10 mg/kg of weight about once to 3 times a day. Drip infusion is also effective. In this case, the total dosage is the same as with injection.

The peptides of the present invention or the pharmaceutically acceptable salts thereof are used as a therapeutic agent such as an anti-endothelin agent. In preparing the therapeutic agent, they are carefully purified so as to contain no bacteria and no pyrogens.

The present invention will be described in more detail with the following Examples, in which all amino acid residues other than glycine take the L-form unless otherwise specified. Table 1 shows the amino acid sequences of endothelin-1, endothelin-2, endothelin-3, mouse endothelin (MET) and novel peptides obtained in Examples of the present invention, compared to one another.

TABLE 1

| | | |
|---|---|---|
| Known | | |
| ET-1 | 1 2 3 4 5 6 7 8 9 10 11 12 13 14 15 16 17<br>CysSerCysSerSerLeuMetAspLysGluCysValTyrPheCysHisLeu-<br>18 19 20 21<br>AspIleIleTrp (SEQ ID NO: 4) | |
| ET-2 | 1 2 3 4 5 6 7 8 9 10 11 12 13 14 15 16 17<br>CysSerCysSerSer<u>TrpLeu</u>AspLysGluCysValTyrPheCysHisLeu-<br>18 19 20 21<br>AspIleIleTrp (SEQ ID NO: 5) | |
| ET-3 | 1 2 3 4 5 6 7 8 9 10 11 12 13 14 15 16 17<br>Cys<u>Thr</u>Cys<u>PheThrTyrLys</u>AspLysGluCysValTyr<u>Tyr</u>CysHisLeu-<br>18 19 20 21<br>AspIleIleTrp (SEQ ID NO: 6) | |
| MET | 1 2 3 4 5 6 7 8 9 10 11 12 13 14 15 16 17<br>CysSerCys<u>AsnSerTrpLeu</u>AspLysGluCysValTyrPheCysHisLeu-<br>18 19 20 21<br>AspIleIleTrp (SEQ ID NO: 7) | |
| Example No. | | |
| 1 | 1 2 3 4 5 6 7 8 9 10 11 12 13 14 15 16 17<br>CysSerCysSerSerLeuMetAspLysGluCysValTyrPheCysHisLeu-<br>18 19 20 21<br><u>ThrLeu</u>IleTrp (SEQ ID NO: 8) (Abbreviation [Thr[18], Leu[19]]-ET-1) | |
| 2 | 1 2 3 4 5 6 7 8 9 10 11 12 13 14 15 16 17<br>CysSerCysSerSerLeuMetAspLysGluCysValTyrPheCysHisLeu-<br>18 19 20 21<br><u>ThrCha</u>IleTrp (SEQ ID NO: 9) (Abbreviation [Thr[18], Cha[19]]-ET-1) | |
| 3 | 1 2 3 4 5 6 7 8 9 10 11 12 13 14 15 16 17<br>CysSerCysSerSerLeuMetAspLysGluCysValTyrPheCysHisLeu-<br>18 19 20 21<br><u>ThrPhe</u>IleTrp (SEQ ID NO: 10) (Abbreviation [Thr[18], Phe[19]]-ET-1) | |
| 4 | 1 2 3 4 5 6 7 8 9 10 11 12 13 14 15 16 17<br>CysSerCysSerSerLeuMetAspLysGluCysValTyrPheCysHisLeu-<br>18 19 20 21<br><u>ThrγLeu</u>IleTrp (SEQ ID NO: 11) (Abbreviation [Thr[18], γLeu[19]]-ET-1) | |
| 5 | 1 2 3 4 5 6 7 8 9 10 11 12 13 14 15 16 17<br>CysSerCysSerSerLeuMetAspLysGluCysValTyrPheCysHisLeu-<br>18 19 20 21<br><u>ThrAsn</u>IleTrp (SEQ ID NO: 12) (Abbreviation [Thr[18], Asn[19]]-ET-1) | |
| 6 | 1 2 3 4 5 6 7 8 9 10 11 12 13 14 15 16 17<br>CysSerCysSerSerLeuMetAspLysGluCysValTyrPheCysHisLeu-<br>18 19 20 21<br><u>SerLeu</u>IleTrp (SEQ ID NO: 13) (Abbreviation [Ser[18], Leu[19]]-ET-1) | |

TABLE 1-continued 7
1 2 3 4 5 6 7 8 9 10 11 12 13 14 15 16 17
CysSerCysSerSerLeuMetAspLysGluCysValTyrPheCysHisLeu- 18 19 20 21
AsnLeuIleTrp (SEQ ID NO: 14) (Abbreviation

[Asn$^{18}$, Leu$^{19}$]-ET-1)

8
1 2 3 4 5 6 7 8 9 10 11 12 13 14 15 16 17
CysSerCysSerSerLeuMetAspLysGluCysValTyrPheCysHisLeu- 18 19 20 21
GlyLeuIleTrp (SEQ ID NO: 15) (Abbreviation

[Gly$^{18}$, Leu$^{19}$]-ET-1)

9
1 2 3 4 5 6 7 8 9 10 11 12 13 14 15 16 17
CysThrCysPheThrTyrLysAspLysGluCysValTyrTyrCysHisLeu- 18 19 20 21
ThrLeuIleTrp (SEQ ID NO: 16) (Abbreviation

[Thr$^{18}$, Leu$^{19}$]-ET-3)

10
1 2 3 4 5 6 7 8 9 10 11 12 13 14 15 16 17
CysSerCysSerSerLeuMetAspAlaGluCysValTyrPheCysHisLeu- 18 19 20 21
ThrLeuIleTrp (SEQ ID NO: 17) (Abbreviation

[Ala$^9$, Thr$^{18}$, Leu$^{19}$]-ET-1)

11
1 2 3 4 5 6 7 8 9 10 11 12 13 14 15 16 17
XaaSerCysSerSerLeuMetAspLysGluCysValTyrPheCysHisLeu- 18 19 20 21
ThrLeuIleTrp (SEQ ID NO: 18) (Wherein Xaa is Mpr.

Abbreviation [Mpr$^1$, Thr$^{18}$, Leu$^{19}$]-ET-1)

12
1 2 3 4 5 6 7 8 9 10 11 12 13 14 15 16 17
CysAlaCysSerSerLeuMetAspLysGluCysValTyrPheCysHisLeu- 18 19 20 21
ThrLeuIleTrp (SEQ ID NO: 19) (Abbreviation

[Ala$^2$, Thr$^{18}$, Leu$^{19}$]-ET-1)

13
1 2 3 4 5 6 7 8 9 10 11 12 13 14 15 16 17
CysSerCysAlaSerLeuMetAspLysGluCysValTyrPheCysHisLeu- 18 19 20 21
ThrLeuIleTrp (SEQ ID NO: 20) (Abbreviation

[Ala$^4$, Thr$^{18}$, Leu$^{19}$]-ET-1)

14
1 2 3 4 5 6 7 8 9 10 11 12 13 14 15 16 17
CysSerCysSerAlaLeuMetAspLysGluCysValTyrPheCysHisLeu- 18 19 20 21
ThrLeuIleTrp (SEQ ID NO: 21) (Abbreviation

[Ala$^5$, Thr$^{18}$, Leu$^{19}$]-ET-1)

15
1 2 3 4 5 6 7 8 9 10 11 12 13 14 15 16 17
CysSerCysSerSerAlaMetAspLysGluCysValTyrPheCysHisLeu- 18 19 20 21
ThrLeuIleTrp (SEQ ID NO: 22) (Abbreviation

[Ala$^6$, Thr$^{18}$, Leu$^{19}$]-ET-1)

16
1 2 3 4 5 6 7 8 9 10 11 12 13 14 15 16 17
CysSerCysSerSerLeuAlaAspLysGluCysValTyrPheCysHisLeu- 18 19 20 21
ThrLeuIleTrp (SEQ ID NO: 23) (Abbreviation

[Ala$^7$, Thr$^{18}$, Leu$^{19}$]-ET-1)

TABLE 1-continued 17    1 2 3 4 5 6 7 8 9 10 11 12 13 14 15 16 17
CysSerCysSerSerLeu<u>Xaa</u>AspLysGluCysValTyrPheCysHisLeu- 18 19 20 21
<u>Thr</u>Leu<u>Ile</u>Trp (SEQ ID NO: 24) (Wherein Xaa is Nle.

Abbreviation [Nle$^7$, Thr$^{18}$, Leu$^{19}$]-ET-1)

18    1 2 3 4 5 6 7 8 9 10 11 12 13 14 15 16 17
CysSerCysSerSer<u>TrpLeu</u>AspLysGluCysValTyrPheCysHisLeu- 18 19 20 21
<u>Thr</u>Leu<u>Ile</u>Trp (SEQ ID NO: 25) (Abbreviation

[Thr$^{18}$, Leu$^{19}$]-ET-2)

In all of the above peptides, Cys$^1$-Cys$^{15}$ (or Mpr$^1$-Cys$^{15}$) and Cys$^3$-Cys$^{11}$ form S—S bonds.

EXAMPLE 1

Production of [Thr$^{18}$, Leu$^{19}$]-ET-1

Using a Boc-Trp(For)-OCH$_2$-Pam resin (0.5 mmole) as a starting material, and Boc-amino acid derivative cartridges (2.0 mmoles) (Applied Biosystems), the Boc groups were eliminated with trifluoroacetic acid, and then, a peptide chain was successively extended from the C-terminal by the HOBt active ester method. Boc-Asp(OcHex) and Boc-Glu(OcHex) were used after the powders manufactured by Peptide Institute Inc. were enclosed in cartridges. In this manner, the protected peptide resin represented by the following formula was obtained:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(-MeBzl)-His(Dnp)-Leu-Thr(Bzl)-Leu-Ile-Trp(For)-OCH$_2$-Pam resin This peptide resin was suspended in 10 ml of DMF, and 1.0 ml of thiophenol was added thereto. The Dnp group, a protective group for the imidazole ring of His, was eliminated by stirring the mixture at room temperature for 2 hours, and the Boc group was further eliminated by treating with 50% TFA/dichloromethane containing 0.1% indole at room temperature for 20 minutes. Then, 500 mg of the peptide resin thus obtained was treated with 5 ml of anhydrous hydrogen fluoride in the presence of 500 mg of p-cresol and 0.75 ml of 1,4-butanedithiol at 0° C. for 1 hour to remove all of the protective groups and to release the peptide from the resin. Hydrogen fluoride was removed under reduced pressure, and ethyl ether was added to the residue to deposit a precipitate. The precipitate was separated by filtration, and 30 ml of TFA was added thereto to dissolve the peptide. The resin was removed by filtration, and the filtrate was concentrated. Ethyl ether was added to the residue to deposit a precipitate. The precipitate was separated by filtration, and dried under reduced pressure. The resulting product was dissolved in 500 ml of 0.1M ammonium acetate/water-nBuOH-EtOH (2:1:1 v/v) (pH 8.0–8.5), and oxidized with air by stirring the solution at room temperature for 15 hours. Then, acetic acid was added thereto to adjust the solution to pH 5.0, and the solvent was removed by distillation under reduced pressure, followed by lyophilization of the residue. The lyophilized product was dissolved in 20 ml of 60% acetic acid. The resulting solution was subjected to a Sephadex G-50 column (5 cm × 108 cm) and eluted with 60% acetic acid. The desired fractions were collected and lyophilized. Finally, the fractions were purified by high performance liquid chromatography using a YMC-D-ODS-5 column (2 cm × 25 cm, YMC CO. Ltd.) to obtain the desired product.

Anal. for amino acids (hydrolysis at 110° C. for 24 hours; numerals in parentheses indicate theoretical values): Asp 1.00(1); Thr 0.93(1); Ser 2.56(3); Glu 1.06(1); Cyt 1.85(2); Val 0.99(1); Met 0.99(1); Ile 0.94(1); Leu 3.08(3); Tyr 0.97(1); Phe 1.02(1); Lys 1.00(1); His 1.19(1)

LSIMS (M+H$^+$)=2477 (theoretical value=2477)

EXAMPLE 2

Production of [Thr$^{18}$, Cha$^{19}$]-ET-1

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(-MeBzl)-His(Dnp)-Leu-Thr(Bzl)-Cha-Ile-Trp(For)-OCH$_2$-Pam resin The resulting peptide resin was further deprotected, oxidized and purified as with Example 1 to obtain the desired product.

Anal. for amino acids: Asp 1.00(1); Thr 0.94(1); Ser 2.55(3); Glu 1.05(1); Cyt 1.69(2); Val 0.97(1); Met 1.01(1); Ile 0.94(1); Leu 2.04(2); Tyr 0.92(1); Phe 1.01(1); Lys 1.00(1); His 1.19(1)

LSIMS (M+H$^+$)=2517 (theoretical value=2517)

EXAMPLE 3

Production of [Thr$^{18}$, Phe$^{19}$]-ET-1

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(-MeBzl)-His(Dnp)-Leu-Thr(Bzl)-Phe-Ile-Trp(For)-O-CH$_2$-Pam resin The resulting peptide resin was further deprotected, oxidized and purified as with Example 1 to obtain the desired product.

Anal. for amino acids: Asp 1.00(1); Thr 0.88(1); Ser 2.45(3); Glu 1.03(1); Cyt 1.48(2); Val 0.88(1); Met 1.00(1); Ile 0.85(1); Leu 1.93(2); Tyr 0.87(1); Phe 1.81(2); Lys 1.01(1); His 0.88(1)

LSIMS (M+H$^+$)=2511 (theoretical value=2511)

EXAMPLE 4

Production of [Thr$^{18}$, γLeu$^{19}$]-ET-1

The following protected peptide resin was obtained by procedures similar to those of Example 1:

Boc-Cys(MeBzl)-Ser(Bzl)-Cys(MeBzl)-Ser(Bzl)-
Ser(Bzl)-Leu-Met-Asp(OcHex)-Lys(ClZ)-Glu(O-
cHex)-Cys(MeBzl)-Val-Tyr(BrZ)-Phe-Cys(-
MeBzl)-His(Dnp)-Leu-Thr(Bzl)-γLeu-Ile-
Trp(For)-OCH$_2$-Pam resin The resulting peptide resin was further deprotected, oxidized and purified as with Example 1 to obtain the desired product.

Anal. for amino acids: Asp 1.00(1); Thr 0.94(1); Ser 2.51(3); Glu 1.05(1); Cyt 1.69(2); Val 0.98(1); Met 1.00(1); Ile 0.92(1); Leu 2.07(2); Tyr 1.04(1); Phe 0.99(1); Lys 1.01(1); His 1.00(1)

LSIMS (M+H+)=2491 (theoretical value=2491)
γLeu=γ-Methyl-L-leucine

EXAMPLE 5

Production of [Thr[18], Asn[19]]-ET-1

The following protected peptide resin was obtained by procedures similar to those of Example 1:
Boc-Cys(MeBzl)-Ser(Bzl)-Cys(MeBzl)-Ser(Bzl)-
Ser(Bzl)-Leu-Met-Asp(OcHex)-Lys(ClZ)-Glu(O-
cHex)-Cys(MeBzl)-Val-Tyr(BrZ)-Phe-Cys(-
MeBzl)-His(Dnp)-Leu-Thr(Bzl)-Asn-Ile-Trp(For)-
OCH$_2$-Pam resin The resulting peptide resin was further deprotected, oxidized and purified as with Example 1 to obtain the desired product.

Anal. for amino acids: Asp 2.00(2); Thr 0.96(1); Ser 2.50(3); Glu 1.07(1); Cyt 0.75(2); Val 0.91(1); Met 1.03(1); Ile 0.91(1); Leu 2.11(2); Tyr 0.92(1); Phe 1.04(1); Lys 1.02(1); His 0.99(1)

LSIMS (M+H+)=2478 (theoretical value=2478)

EXAMPLE 6

Production of [Ser[18], Leu[19]]-ET-1

The following protected peptide resin was obtained by procedures similar to those of Example 1:
Boc-Cys(MeBzl)-Ser(Bzl)-Cys(MeBzl)-Ser(Bzl)-
Ser(Bzl)-Leu-Met-Asp(OcHex)-Lys(ClZ)-Glu(O-
cHex)-Cys(MeBzl)-Val-Tyr(BrZ)-Phe-Cys(-
MeBzl)-His(Dnp)-Leu-Ser(Bzl)-Leu-Ile-Trp(For)-
OCH$_2$-Pam resin The resulting peptide resin was further deprotected, oxidized and purified as with Example 1 to obtain the desired product.

Anal. for amino acids: Asp 1.00(1); Ser 3.39(4); Glu 1.06(1); Cyt 1.58(2); Val 0.90(1); Met 0.98(1); Ile 0.87(1); Leu 3.05(3); Tyr 0.87(1); Phe 0.98(1); Lys 0.99(1); His 0.93(1)

LSIMS (M+H+)=2463 (theoretical value=2463)

EXAMPLE 7

Production of [Asn[18], Leu[19]]-ET-1

The following protected peptide resin was obtained by procedures similar to those of Example 1:
Boc-Cys(MeBzl)-Ser(Bzl)-Cys(MeBzl)-Ser(Bzl)-
Ser(Bzl)-Leu-Met-Asp(OcHex)-Lys(ClZ)-Glu(O-
cHex)-Cys(MeBzl)-Val-Tyr(BrZ)-Phe-Cys(-
MeBzl)-His(Dnp)-Leu-Asn-Leu-Ile-Trp(For)-
OCH$_2$-Pam resin The resulting peptide resin was further deprotected, oxidized and purified as with Example 1 to obtain the desired product.

Anal. for amino acids: Asp 2.00(2); Set 2.40(3); Glu 1.04(1); Cyt 0.76(2); Val 0.85(1); Met 1.02(1); Ile 0.85(1); Leu 3.06(3); Tyr 0.85(1); Phe 1.00(1); Lys 1.00(1); His 0.93(1)

LSIMS (M+H+)=2490 (theoretical value=2490)

EXAMPLE 8

Production of [Gly[18], Leu[19]]-ET-1

The following protected peptide resin was obtained by procedures similar to those of Example 1:
Boc-Cys(MeBzl)-Ser(Bzl)-Cys(MeBzl)-Ser(Bzl)-
Ser(Bzl)-Leu-Met-Asp(OcHex)-Lys(ClZ)-Glu(O-
cHex)-Cys(MeBzl)-Val-Tyr(BrZ)-Phe-Cys(-
MeBzl)-His(Dnp)-Leu-Gly-Leu-Ile-Trp(For)-
OCH$_2$-Pam resin The resulting peptide resin was further deprotected, oxidized and purified as with Example 1 to obtain the desired product.

Anal. for amino acids: Asp 1.00(1); Ser 2.51(3); Glu 1.05(1); Gly 0.99(1); Cyt 1.48(2); Val 0.89(1); Met 0.98(1); Ile 0.84(1); Leu 3.01(3); Tyr 0.86(1); Phe 0.97(1); Lys 0.99(1); His 0.93(1)

LSIMS (M+H+)=2433 (theoretical value=2433)

EXAMPLE 9

Production of [Thr[18], Leu[19]]-ET-3

The following protected peptide resin was obtained by procedures similar to those of Example 1:
Boc-Cys(MeBzl)-Thr(Bzl)-Cys(MeBzl)-Phe-
Thr(Bzl)-Tyr(BrZ)-Lys(ClZ)-Asp(OcHex)-
Lys(ClZ)-Glu(OcHex)-Cys(MeBzl)-Val-
Tyr(BrZ)-Tyr(BrZ)-Cys(MeBzl)-His(Dnp)-Leu-
Thr(Bzl)-Leu-Ile-Trp(For)-OCH$_2$-Pam resin The resulting peptide resin was further deprotected, oxidized and purified as with Example 1 to obtain the desired product.

Anal. for amino acids: Asp 1.00(1); Thr 2.71(3); Glu 1.10(1); Cyt 0.77(2); Val 0.94(1); Ile 0.91(1); Leu 2.01(2); Tyr 2.84(3); Phe 0.99(1); Lys 1.96(2); His 0.95(1)

LSIMS (M+H+)=2628 (theoretical value=2628)

EXAMPLE 10

Production of [Ala[9], Thr[18], Leu[19]]-ET-1

The following protected peptide resin was obtained by procedures similar to those of Example 1:
Boc-Cys(MeBzl)-Ser(Bzl)-Cys(MeBzl)-Ser(Bzl)-
Ser(Bzl)-Leu-Met-Asp(OcHex)-Ala-Glu(OcHex)-
Cys(MeBzl)-Val-Tyr(BrZ)-Phe-Cys(MeBzl)-
His(Dnp)-Leu-Thr(Bzl)-Leu-Ile-Trp(For)-OCH$_2$-
Pam resin The resulting peptide resin was further deprotected, oxidized and purified as with Example 1 to obtain the desired product.

Anal. for amino acids: Asp 1.00(1); Thr 0.91(1); Ser 2.46(3); Glu 1.03(1); Ala 0.99(1); Cyt 0.75(2); Val 0.88(1); Met 1.00(1); Ile 0.88(1); Leu 2.98(3); Tyr 0.86(1); Phe 0.96(1); His 0.93(1)

LSIMS (M+H+)=2420 (theoretical value=2420)

EXAMPLE 11

Production of [Mpr[1], Thr[18], Leu]-ET-1

The following protected peptide resin was obtained by procedures similar to those of Example 1:
Mpr(MeBzl)-Ser(Bzl)-Cys(MeBzl)-Ser(Bzl)-
Ser(Bzl)-Leu-Met-Asp(OcHex)-Lys(ClZ)-Glu(O-
cHex)-Cys(MeBzl)-Val-Tyr(BrZ)-Phe-Cys(-
MeBzl)-His(Dnp)-Leu-Thr(Bzl)-Leu-Ile-Trp(For)-
OCH$_2$-Pam resin The resulting peptide resin was further deprotected, oxidized and purified as with Example 1 to obtain the desired product.

Anal. for amino acids: Asp 1.00(1); Thr 0.94(1); Ser 2.53(3); Glu 1.07(1); Cyt 0.66(1); Val 0.94(1); Met 0.98(1); Ile 0.92(1); Leu 3.03(3); Tyr 0.88(1); Phe 0.97(1); Lys 0.98(1); His 0.94(1)

LSIMS (M+H$^+$)=2462 (theoretical value=2462)

EXAMPLE 12

Production of [Ala$^2$, Thr$^{18}$, Leu$^{19}$]-ET-1

The following protected peptide resin was obtained by procedures similar to those of Example 1:
Boc-Cys(MeBzl)-Ala-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Thr(Bzl)-Leu-Ile-Trp(For)-OCH$_2$-Pam resin The resulting peptide resin was further deprotected, oxidized and purified as with Example 1 to obtain the desired product.

Anal. for amino acids: Asp 1.00(1); Thr 0.95(1); Ser 1.74(2); Glu 1.06(1); Ala 0.96(1); Cyt 0.74(2); Val 0.95(1); Met 0.99(1); Ile 0.94(1); Leu 3.08(3); Tyr 0.89(1); Phe 0.98(1); Lys 0.99(1); His 0.96(1)

LSIMS (M+H$^+$)=2461 (theoretical value=2461)

EXAMPLE 13

Production of [Ala$^4$, Thr$^{18}$, Leu$^{19}$]-ET-1

The following protected peptide resin was obtained by procedures similar to those of Example 1:
Boc-Cys(MeBzl)-Ser(Bzl)-Cys(MeBzl)-Ala-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Thr(Bzl)-Leu-Ile-Trp(For)-OCH$_2$-Pam resin The resulting peptide resin was further deprotected, oxidized and purified as with Example 1 to obtain the desired product.

Anal. for amino acids: Asp 1.00(1); Thr 0.95(1); Ser 1.67(2); Glu 1.06(1); Ala 0.96(1); Cyt 0.82(2); Val 0.94(1); Met 0.99(1); Ile 0.92(1); Leu 3.06(3); Tyr 0.88(1); Phe 0.98(1); Lys 0.99(1); His 0.95(1)

LSIMS (M+H$^+$)=2461 (theoretical value=2461)

EXAMPLE 14

Production of [Ala$^5$, Thr$^{18}$, Leu$^{19}$]-ET-1

The following protected peptide resin was obtained by procedures similar to those of Example 1:
Boc-CYs(MeBzl)-Ser(Bzl)-Cys(MeBzl)-Ser(Bzl)-Ala-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Thr(Bzl)-Leu-Ile-Trp(For)-OCH$_2$-Pam resin The resulting peptide resin was further deprotected, oxidized and purified as with Example 1 to obtain the desired product.

Anal. for amino acids: Asp 1.00(1); Thr 0.94(1); Ser 1.68(2); Glu 1.05(1); Ala 0.98(1); Cyt 0.92(2); Val 0.92(1); Met 0.92(1); Ile 0.90(1); Leu 2.96(3); Tyr 0.91(1); Phe 0.98(1); Lys 0.98(1); His 0.95(1)

LSIMS (M+H$^+$)=2461 (theoretical value=2461)

EXAMPLE 15

Production of [Ala$^6$, Thr$^{18}$, Leu$^{19}$]-ET-1

The following protected peptide resin was obtained by procedures similar to those of Example 1:
Boc-Cys(MeBzl)-Ser(Bzl)-Cys(MeBzl)-Ser(Bzl)-Ser(Bzl)-Ala-Met-Asp(OcHex)-Lys(ClZ)-Glu(OcHex)-Cys(MeBzl)-Val-Tyr(BrZ)-Phe-Cys(MeBzl)-His(Dnp)-Leu-Thr(Bzl)-Leu-Ile-Trp(For)-OCH$_2$-Pam resin The resulting peptide resin was further deprotected, oxidized and purified as with Example 1 to obtain the desired product.

Anal. for amino acids: Asp 1.00(1); Thr 0.89(1); Ser 2.45(3); Glu 1.04(1); Ala 0.98(1); Cyt 0.88(2); Val 0.86(1); Met 0.96(1); Ile 0.85(1); Leu 1.85(2); Tyr 0.86(1); Phe 0.93(1); Lys 0.98(1); His 0.90(1)

LSIMS (M+H$^+$)=2435 (theoretical value=2435)

EXAMPLE 16

Production of [Ala$^7$, Thr$^{18}$, Leu$^{19}$]-ET-1

The following protected peptide resin was obtained by procedures similar to those of Example 1:
Boc-Cys(MeBzl)-Ser(Bzl)-Cys(MeBzl)-Ser(Bzl)-Ser(Bzl)-Leu-Ala-Asp(OcHex)-Lys(ClZ)-Glu(OcHex)-Cys(MeBzl)-Val-Tyr(BrZ)-Phe-Cys(MeBzl)-His(Dnp)-Leu-Thr(Bzl)-Leu-Ile-Trp(For)-OCH$_2$-Pam resin The resulting peptide resin was further deprotected, oxidized and purified as with Example 1 to obtain the desired product.

Anal. for amino acids: Asp 1.00(1); Thr 0.94(1); Ser 2.55(3); Glu 1.06(1); Ala 0.97(1); Cyt 0.87(2); Val 0.93(1); Ile 0.92(1); Leu 3.03(3); Tyr 0.90(1); Phe 0.98(1); Lys 0.98(1); His 0.95(1)

LSIMS (M+H$^+$)=2417 (theoretical value=2417)

EXAMPLE 17

Production of [Nle$^7$, Thr$^{18}$, Leu$^{19}$]-ET-1

The following protected peptide resin was obtained by procedures similar to those of Example 1:
Boc-Cys(MeBzl)-Ser(Bzl)-Cys(MeBzl)-Ser(Bzl)-Ser(Bzl)-Leu-Nle-Asp(OcHex)-Lys(ClZ)-Glu(OcHex)-Cys(MeBzl)-Val-Tyr(BrZ)-Phe-Cys(MeBzl)-His(Dnp)-Leu-Thr(Bzl)-Leu-Ile-Trp(For)-OCH$_2$-Pam resin The resulting peptide resin was further deprotected, oxidized and purified as with Example 1 to obtain the desired product.

Anal. for amino acids: Asp 1.00(1); Thr 0.95(1); Ser 2.50(3); Glu 1.07(1); Cyt 0.78(2); Val 0.95(1); Ile 0.93(1); Leu 3.07(3); Tyr+Nle 1.97(2); Phe 0.99(1); Lys 0.99(1); His 0.96(1)

LSIMS (M+H$^+$)=2459 (theoretical value=2459)

EXAMPLE 18

Production of [Thr$^{18}$, Leu$^{19}$]-ET-2

The following protected peptide resin was obtained by procedures similar to those of Example 1:
Boc-Cys(MeBzl)-Ser(Bzl)-Cys(MeBzl)-Ser(Bzl)-Ser(Bzl)-Trp(For)-Leu-Asp(OcHex)-Lys(ClZ)-Glu(OcHex)-Cys(MeBzl)-Val-Tyr(BrZ)-Phe-Cys(MeBzl)-His(Dnp)-Leu-Thr(Bzl)-Leu-Ile-Trp(For)-OCH$_2$-Pam resin The resulting peptide resin was further deprotected, oxidized and purified as with Example 1 to obtain the desired product.

LSIMS (M+H+)=2532 (theoretical value=2532)

Experimental Example (1) Assay of Constrictor Suppressing Activity on Porcine Coronary Smooth Muscles Spiral strips 2 mm×15 mm prepared from the coronary right ramus circumflexus from which the adventitial connective tissues and the endothelial cells were removed were set to 4 ml organ baths. The tension of each strip was detected by a force displacement transducer UL-10GR (Minebea), and recorded by a polygraph (NEC Sanei). The organ baths were maintained at 37° C., and filled with a Krebs-Henseleit solution (composition: 118 mM NaCl, 4.7 mM KCl, 2.5 mM $CaCl_2$, 1.2 mM $KH_2PO_4$, 25.0 mM $NaHCO_3$, 1.2 mM $MgSO_4$, 10.0 mM glucose) gassed with 95% $O_2$ and 5% $CO_2$.

A tension of 1.25 to 1.5 g was applied to each of the strips, followed by equilibration for 1.5 hours. 60 mM KCl was repeatedly applied thereto at intervals of 30 minutes until the constriction response became constant. After additional equilibration for 1.5 hours, a sample for assay was given thereto. The constriction of the strips was normalized by the constriction response of the individual strips to 60 mM KCl and statistically processed.

The suppressing activity was determined as a $pA_2$ value by giving endothelin-1 cumulatively about 15 minutes after the compound having a predetermined concentration was given, and comparing the constriction thereof with that of a control sample in which only endothelin-1 was given. Results thereof are shown in Table 3.

The novel peptides of the present invention represented by formula (I) and the salts thereof showed the activity of suppressing the constriction due to endothelin in porcine coronary smooth muscles. Such a case has not been reported yet. Hence, the peptides of the present invention represented by formula (I) or the salts thereof can be used for the treatment of hypertension, cardiac infarction, acute renal insufficiency or asthma of mammals such as mice, rats, rabbits, dogs, cats, pigs and humans.

(2) As to the antagonistic property of the peptides of the present invention to endothelin, the affinity for an endothelin receptor and the constrictor activity on porcine coronary smooth muscles (according to the method described in (1) described above) were assayed. Results thereof are shown in Table 2. The affinity for the receptor was assayed by the following method.

Assay of Affinity for Receptor

A membrane fraction prepared from the porcine heart was diluted to 0.15 mg/ml by using a buffer solution for assay, and 100 μl of the resulting suspension of the membrane fraction was poured into each assay tube to use for assay. To this suspension of the membrane fraction was added 2 μl of 5 nM $^{125}I$ labeled endothelin-1 solution. Further, 3 μl of a test peptide solution was added thereto, followed by incubation at a temperature of 25° C. for 1 hour. Then, the resulting suspension was diluted with 900 μl of the buffer solution for assay cooled with ice, and thereafter separated into a supernatant and a precipitate by centrifugation at 12,000×g for 10 minutes. Cell membranes and an endothelin receptor embedded therein were contained in the precipitate, and radioactive iodine-labeled endothelin combined with the receptor was also recovered in the precipitate. Accordingly, the amount of radioactive iodine-labeled endothelin combined with the endothelin receptor was determined by measuring the amount of radioactive iodine contained in the precipitate with a gamma-ray counter. As shown in Table 2, the peptides of the present invention are high in the affinity for the endothelin receptor and not high in the maximum constriction. The results reveals that the peptides of the the present invention have strong antagonistic activity.

TABLE 2

| Example No. | Compound ET-1 | Receptor binding activity[1] (specific activity) 100[3] | Constrictor activity[2] (specific activity) 100[4] | Maximum constriction (% 60 mM KCl) 120 |
|---|---|---|---|---|
| 1 | [Thr18, Leu19]-ET-1 | 40 | <0.1 | 4 |
| 2 | [Thr18, Cha19]-ET-1 | 23 | <0.1 | 2 |
| 3 | [Thr18, Phe19]-ET-1 | 9.0 | <0.1 | 4 |
| 4 | [Thr18, γLeu19]-ET-1 | 23 | <0.1 | 0 |
| 5 | [Thr18, Asn19]-ET-1 | 1.6 | <0.1 | 9 |
| 6 | [Ser18, Leu19]-ET-1 | 15 | <0.1 | 1 |
| 7 | [Asn18, Leu19]-ET-1 | 12 | <0.1 | 4 |
| 8 | [Gly18, Leu19]-ET-1 | 9.5 | <0.1 | 14 |
| 9 | [Thr18, Leu19]-ET-3 | 4.0 | <0.1 | 12 |
| 10 | [Ala9, Thr18, Leu19]-ET-1 | 16 | <0.1 | 4 |
| 11 | [Mpr1, Thr18, Leu19]-ET-1 | 16 | <0.1 | 1 |
| 12 | [Ala2, Thr18, Leu19]-ET-1 | 32 | <0.1 | 5 |
| 13 | [Ala4, Thr18, Leu19]-ET-1 | 57 | <0.1 | 6 |
| 14 | [Ala5, Thr18, Leu19]-ET-1 | 8.6 | <0.1 | 6 |
| 15 | [Ala6, Thr18, Leu19]-ET-1 | 11 | <0.1 | 7 |
| 16 | [Ala7, Thr18, Leu19]-ET-1 | 62 | <0.1 | 9 |
| 17 | [Nle7, Thr18, Leu19]-ET-1 | 27 | <0.1 | 9 |

[1] Porcine myocardial membrane fraction
[2] Porcine coronary artery
[3] $IC_{50} = 2.0 \times 10^{-9}$ M, $IC_{50}$ represents the concentration of a sample required to prevent 50% of the binding of $I^{125}$-ET-1 to the porcine myocardial membrane fraction.
[4] $EC_{50}$ (% KCl) = 1.6 × 10$^{-9}$ M, $EC_{50}$ (% KCl) represents the concentration of a sample which induces 50% of the constriction of the porcine coronary artery due to 60 mM KCl.

(3) The antagonistic activity on the constriction of porcine coronary smooth muscles are shown in Table 3 below.

TABLE 3

Antagonistic activity on the construction of porcine coronary smooth muscles

| Example No. | Compound | pA2 | Relative potency |
|---|---|---|---|
| 1 | [Thr18, Leu19]-ET-1 | 7.7 | 100 |
| 2 | [Thr18, Cha19]-ET-1 | 7.7 | 100 |
| 3 | [Thr18, Phe19]-ET-1 | 7.2 | 32 |
| 4 | [Thr18, γLeu19]-ET-1 | 7.4 | 50 |
| 6 | [Ser18, Leu19]-ET-1 | 7.5 | 63 |
| 8 | [Gly18, Leu19]-ET-1 | 6.7 | 10 |
| 10 | [Ala9, Thr18, Leu19]-ET-1 | 5.9 | 1.6 |
| 11 | [Mpr1, Thr18, Leu19]-ET-1 | 6.5 | 6 |

TABLE 3-continued

Antagonistic activity on the construction of porcine coronary smooth muscles

| Example No. | Compound | pA$_2$ | Relative potency |
|---|---|---|---|
| 12 | [Ala$^2$, Thr$^{18}$, Leu$^{19}$]-ET-1 | 6.7 | 10 |
| 13 | [Ala$^4$, Thr$^{18}$, Leu$^{19}$]-ET-1 | 6.9 | 16 |
| 14 | [Ala$^5$, Thr$^{18}$, Leu$^{19}$]-ET-1 | 5.5 | 0.6 |
| 15 | [Ala$^6$, Thr$^{18}$, Leu$^{19}$]-ET-1 | 6.5 | 6 |
| 16 | [Ala$^7$, Thr$^{18}$, Leu$^{19}$]-ET-1 | 7.2 | 32 | pA$_2$ is a negative logarithm value of a molar concentration of a competitive antagonist necessary for shifting in parallel a dose response curve for an active drug (for example, ET-1) alone to the high dose side by a factor of 2. The higher value shows the stronger antagonistic activity.

As described above, the peptides of the present invention represented by formula (1) and the salts thereof have the antagonistic property to endothelin, so that they can be used as agents for improving circulatory functions, vasodilators or therapeutic agents for asthma.

---

What is claimed is:

1. An endothelin-1 (ET-1) analog, which is selected from the group of ET-1 analogs consisting of peptides having the formula of SEQ ID NO:8, SEQ ID NO:9, SEQ ID NO:10, SEQ ID NO:11, SEQ ID NO:13, SEQ ID NO:14, SEQ ID NO:16, SEQ ID NO:17, SEQ ID NO:18, SEQ ID NO:19, SEQ ID NO:20, SEQ ID NO:23, SEQ ID NO:24, and SEQ ID NO:25 or a pharmaceutically-acceptable salt thereof.

2. The ET-1 analog of claim 1, which is SEQ ID NO:8.

3. The ET-1 analog of claim 1, which is SEQ ID NO:9.

4. The ET-1 analog of claim 1, which is SEQ ID NO:11.

5. A pharmaceutical composition comprising the peptide or the pharmaceutically acceptable salt thereof claimed in claim 1.

6. A method for bringing about an antagonistic activity to an endothelin receptor in a warm-blooded animal, which comprises administering an effective amount of the peptide or the pharmaceutically acceptable salt thereof claimed in claim 1 to the warm-blooded animal.

7. A pharmaceutical composition according to claim 5, which is selected from the group of ET-1 analogs consisting of peptides having the formula of SEQ ID NO:8, SEQ ID NO:9, SEQ ID NO:11, SEQ ID NO:13, SEQ ID NO:20, SEQ ID NO:23, SEQ ID NO:24, SEQ ID NO:17, SEQ ID NO:18 and SEQ ID NO:19 or a pharmaceutically-acceptable salt thereof, which is used as an antagonistic composition to an endothelin receptor.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:1:

```
Xaa  Xaa  Cys  Xaa  Xaa  Xaa  Xaa  Asp  Xaa  Glu  Cys  Val  Tyr  Xaa  Cys  His
1                 5                         10                           15

Xaa  Xaa  Xaa  Ile  Xaa
                20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Xaa  Xaa  Cys  Xaa  Xaa  Xaa  Xaa  Asp  Xaa  Glu  Cys  Val  Tyr  Xaa  Cys  His
1                 5                         10                           15

Xaa  Xaa  Xaa  Ile  Xaa
                20
```

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond (B) LOCATION: 3,11

(xi) SEQUENCE DESCRIPTION: SEQ ID NO:3:

```
Cys Xaa Cys Xaa Xaa Xaa Xaa Asp Lys Glu Cys Val Tyr Xaa Cys His
1               5                   10                  15
Leu Asp Ile Ile Trp
            20
```

(2) INFORMATION FOR SEQ ID NO:4:

(i) SEQUENCE CHARACTERISTICS:
        (A) LENGTH: 21 amino acids
        (B) TYPE: amino acid
        (D) TOPOLOGY: linear (ii) MOLECULE TYPE: protein (ix) FEATURE:
        (A) NAME/KEY: Disulfide-bond
        (B) LOCATION: 1,15

(ix) FEATURE:
        (A) NAME/KEY: Disulfide-bond
        (B) LOCATION: 3,11

(xi) SEQUENCE DESCRIPTION: SEQ ID NO:4:

```
Cys Ser Cys Ser Ser Leu Met Asp Lys Glu Cys Val Tyr Phe Cys His
1               5                   10                  15
Leu Asp Ile Ile Trp
            20
```

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear (ii) MOLECULE TYPE: protein (ix) FEATURE:
        (A) NAME/KEY: Disulfide-bond
        (B) LOCATION: 1,15

(ix) FEATURE:
        (A) NAME/KEY: Disulfide-bond
        (B) LOCATION: 3,11

(xi) SEQUENCE DESCRIPTION: SEQ ID NO:5:

```
Cys Ser Cys Ser Ser Trp Leu Asp Lys Glu Cys Val Tyr Phe Cys His
1               5                   10                  15
Leu Asp Ile Ile Trp
            20
```

(2) INFORMATION FOR SEQ ID NO:6:

(i) SEQUENCE CHARACTERISTICS:
        (A) LENGTH: 21 amino acids
        (B) TYPE: amino acid
        (D) TOPOLOGY: linear (ii) MOLECULE TYPE: protein (ix) FEATURE:
        (A) NAME/KEY: Disulfide-bond
        (B) LOCATION: 1,15

(ix) FEATURE:
        (A) NAME/KEY: Disulfide-bond
        (B) LOCATION: 3,11

(xi) SEQUENCE DESCRIPTION: SEQ ID NO:6:

```
Cys  Thr  Cys  Phe  Thr  Tyr  Lys  Asp  Lys  Glu  Cys  Val  Tyr  Tyr  Cys  His
1              5                        10                       15

Leu  Asp  Ile  Ile  Trp
              20
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:7:

```
Cys  Ser  Cys  Asn  Ser  Trp  Leu  Asp  Lys  Glu  Cys  Val  Tyr  Phe  Cys  His
1              5                        10                       15

Leu  Asp  Ile  Ile  Trp
              20
```

( 2 ) INFORMATION FOR SEQ ID NO:8:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:8:

```
Cys  Ser  Cys  Ser  Ser  Leu  Met  Asp  Lys  Glu  Cys  Val  Tyr  Phe  Cys  His
1              5                        10                       15

Leu  Thr  Leu  Ile  Trp
              20
```

( 2 ) INFORMATION FOR SEQ ID NO:9:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:9:

```
Cys  Ser  Cys  Ser  Ser  Leu  Met  Asp  Lys  Glu  Cys  Val  Tyr  Phe  Cys  His
1              5                        10                       15

Leu  Thr  Xaa  Ile  Trp
```

(2) INFORMATION FOR SEQ ID NO:10:

(i) SEQUENCE CHARACTERISTICS:
        (A) LENGTH: 21 amino acids
        (B) TYPE: amino acid
        (D) TOPOLOGY: linear (ii) MOLECULE TYPE: protein (ix) FEATURE:
        (A) NAME/KEY: Disulfide-bond
        (B) LOCATION: 1,15

(ix) FEATURE:
        (A) NAME/KEY: Disulfide-bond
        (B) LOCATION: 3,11

(xi) SEQUENCE DESCRIPTION: SEQ ID NO:10:

```
Cys  Ser  Cys  Ser  Ser  Leu  Met  Asp  Lys  Glu  Cys  Val  Tyr  Phe  Cys  His
1                   5                        10                            15

Leu  Thr  Phe  Ile  Trp
                20
```

(2) INFORMATION FOR SEQ ID NO:11:

(i) SEQUENCE CHARACTERISTICS:
        (A) LENGTH: 21 amino acids
        (B) TYPE: amino acid
        (D) TOPOLOGY: linear (ii) MOLECULE TYPE: protein (ix) FEATURE:
        (A) NAME/KEY: Disulfide-bond
        (B) LOCATION: 1,15

(ix) FEATURE:
        (A) NAME/KEY: Disulfide-bond
        (B) LOCATION: 3,11

(ix) FEATURE:
        (A) NAME/KEY: Modified site
        (B) LOCATION: 19
        (C) OTHER INFORMATION: Leu (xi) SEQUENCE DESCRIPTION: SEQ ID NO:11:

```
Cys  Ser  Cys  Ser  Ser  Leu  Met  Asp  Lys  Glu  Cys  Val  Tyr  Phe  Cys  His
1                   5                        10                            15

Leu  Thr  Xaa  Ile  Trp
                20
```

(2) INFORMATION FOR SEQ ID NO:12:

(i) SEQUENCE CHARACTERISTICS:
        (A) LENGTH: 21 amino acids
        (B) TYPE: amino acid
        (D) TOPOLOGY: linear (ii) MOLECULE TYPE: protein (ix) FEATURE:
        (A) NAME/KEY: Disulfide-bond
        (B) LOCATION: 1,15

(ix) FEATURE:
        (A) NAME/KEY: Disulfide-bond
        (B) LOCATION: 3,11

(xi) SEQUENCE DESCRIPTION: SEQ ID NO:12:

```
Cys  Ser  Cys  Ser  Ser  Leu  Met  Asp  Lys  Glu  Cys  Val  Tyr  Phe  Cys  His
1                   5                        10                            15
```

```
     Leu Thr Asn Ile Trp
              20
```

( 2 ) INFORMATION FOR SEQ ID NO:13:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:13:

```
Cys Ser Cys Ser Ser Leu Met Asp Lys Glu Cys Val Tyr Phe Cys His
1               5                   10                  15

Leu Ser Leu Ile Trp
             20
```

( 2 ) INFORMATION FOR SEQ ID NO:14:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:14:

```
Cys Ser Cys Ser Ser Leu Met Asp Lys Glu Cys Val Tyr Phe Cys His
1               5                   10                  15

Leu Asn Leu Ile Trp
             20
```

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:15:

```
 Cys Ser Cys Ser Ser Leu Met Asp Lys Glu Cys Val Tyr Phe Cys His
1               5                   10                  15

Leu Gly Leu Ile Trp
              20
```

( 2 ) INFORMATION FOR SEQ ID NO:16:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:16:

```
Cys Thr Cys Phe Thr Tyr Lys Asp Lys Glu Cys Val Tyr Tyr Cys His
1               5                   10                  15
Leu Thr Leu Ile Trp
                20
```

( 2 ) INFORMATION FOR SEQ ID NO:17:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( x i ) SEQUENCE DESCRIPTION: SEQ ID NO:17:

```
Cys Ser Cys Ser Ser Leu Met Asp Ala Glu Cys Val Tyr Phe Cys His
1               5                   10                  15
Leu Thr Leu Ile Trp
                20
```

( 2 ) INFORMATION FOR SEQ ID NO:18:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: Disulfide-bond
        ( B ) LOCATION: 1,15

( i x ) FEATURE:
        ( A ) NAME/KEY: Disulfide-bond
        ( B ) LOCATION: 3,11

( i x ) FEATURE:
        ( A ) NAME/KEY: Modified site
        ( B ) LOCATION: 1
        ( C ) OTHER INFORMATION: Mpr ( x i ) SEQUENCE DESCRIPTION: SEQ ID NO:18:

```
Xaa Ser Cys Ser Ser Leu Met Asp Lys Glu Cys Val Tyr Phe Cys His
1               5                   10                  15
Leu Thr Leu Ile Trp
                20
```

( 2 ) INFORMATION FOR SEQ ID NO:19:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: protein ( i x ) FEATURE:
    ( A ) NAME/KEY: Disulfide-bond
    ( B ) LOCATION: 1,15

( i x ) FEATURE:
    ( A ) NAME/KEY: Disulfide-bond
    ( B ) LOCATION: 3,11

( x i ) SEQUENCE DESCRIPTION: SEQ ID NO:19:

```
Cys  Ala  Cys  Ser  Ser  Leu  Met  Asp  Lys  Glu  Cys  Val  Tyr  Phe  Cys  His
1                   5                        10                            15

Leu  Thr  Leu  Ile  Trp
               20
```

( 2 ) INFORMATION FOR SEQ ID NO:20:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: protein ( i x ) FEATURE:
    ( A ) NAME/KEY: Disulfide-bond
    ( B ) LOCATION: 1,15

( i x ) FEATURE:
    ( A ) NAME/KEY: Disulfide-bond
    ( B ) LOCATION: 3,11

( x i ) SEQUENCE DESCRIPTION: SEQ ID NO:20:

```
Cys  Ser  Cys  Ala  Ser  Leu  Met  Asp  Lys  Glu  Cys  Val  Tyr  Phe  Cys  His
1                   5                        10                            15

Leu  Thr  Leu  Ile  Trp
               20
```

( 2 ) INFORMATION FOR SEQ ID NO:21:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: protein ( i x ) FEATURE:
    ( A ) NAME/KEY: Disulfide-bond
    ( B ) LOCATION: 1,15

( i x ) FEATURE:
    ( A ) NAME/KEY: Disulfide-bond
    ( B ) LOCATION: 3,11

( x i ) SEQUENCE DESCRIPTION: SEQ ID NO:21:

```
Cys  Ser  Cys  Ser  Ala  Leu  Met  Asp  Lys  Glu  Cys  Val  Tyr  Phe  Cys  His
1                   5                        10                            15

Leu  Thr  Leu  Ile  Trp
               20
```

( 2 ) INFORMATION FOR SEQ ID NO:22:

( i ) SEQUENCE CHARACTERISTICS:

(A) LENGTH: 21 amino acids
(B) TYPE: amino acid
(D) TOPOLOGY: linear (i i) MOLECULE TYPE: protein (i x) FEATURE:
    (A) NAME/KEY: Disulfide-bond
    (B) LOCATION: 1,15

(i x) FEATURE:
    (A) NAME/KEY: Disulfide-bond
    (B) LOCATION: 3,11

(x i) SEQUENCE DESCRIPTION: SEQ ID NO:22:

Cys Ser Cys Ser Ser Ala Met Asp Lys Glu Cys Val Tyr Phe Cys His
1               5                   10                  15

Leu Thr Leu Ile Trp
                20

(2) INFORMATION FOR SEQ ID NO:23:

(i) SEQUENCE CHARACTERISTICS:
    (A) LENGTH: 21 amino acids
    (B) TYPE: amino acid
    (D) TOPOLOGY: linear (i i) MOLECULE TYPE: protein (i x) FEATURE:
    (A) NAME/KEY: Disulfide-bond
    (B) LOCATION: 1,15

(i x) FEATURE:
    (A) NAME/KEY: Disulfide-bond
    (B) LOCATION: 3,11

(x i) SEQUENCE DESCRIPTION: SEQ ID NO:23:

Cys Ser Cys Ser Ser Leu Ala Asp Lys Glu Cys Val Tyr Phe Cys His
1               5                   10                  15

Leu Thr Leu Ile Trp
                20

(2) INFORMATION FOR SEQ ID NO:24:

(i) SEQUENCE CHARACTERISTICS:
    (A) LENGTH: 21 amino acids
    (B) TYPE: amino acid
    (D) TOPOLOGY: linear (i i) MOLECULE TYPE: protein (i x) FEATURE:
    (A) NAME/KEY: Disulfide-bond
    (B) LOCATION: 1,15

(i x) FEATURE:
    (A) NAME/KEY: Disulfide-bond
    (B) LOCATION: 3,11

(i x) FEATURE:
    (A) NAME/KEY: Modified-site
    (B) LOCATION: 7
    (C) OTHER INFORMATION: Nle (x i) SEQUENCE DESCRIPTION: SEQ ID NO:24:

Cys Ser Cys Ser Ser Leu Xaa Asp Lys Glu Cys Val Tyr Phe Cys His
1               5                   10                  15

Leu Thr Leu Ile Trp
                20

(2) INFORMATION FOR SEQ ID NO:25:

( i ) SEQUENCE CHARACTERISTICS:
  ( A ) LENGTH: 21 amino acids
  ( B ) TYPE: amino acid
  ( D ) TOPOLOGY: linear ( i i ) MOLECULE TYPE: protein ( i x ) FEATURE:
  ( A ) NAME/KEY: Disulfide-bond
  ( B ) LOCATION: 1,15

( i x ) FEATURE:
  ( A ) NAME/KEY: Disulfide-bond
  ( B ) LOCATION: 3,11

( x i ) SEQUENCE DESCRIPTION: SEQ ID NO:25:

Cys Ser Cys Ser Ser Trp Leu Asp Lys Glu Cys Val Tyr Phe Cys His
1               5                   10                  15

Leu Thr Leu Ile Trp
            20